United States Patent
Luce et al.

[11] Patent Number: 5,381,196
[45] Date of Patent: Jan. 10, 1995

[54] CONTRAST SENSITIVITY TESTER

[75] Inventors: David A. Luce, Clarence Center, N.Y.; Bernard Grolman, Worcester, Mass.

[73] Assignee: Leica Inc., Depew, N.Y.

[21] Appl. No.: 90,541

[22] Filed: Jul. 13, 1993

[51] Int. Cl.⁶ .......................... A61B 3/02; A61B 3/032
[52] U.S. Cl. ................................ 351/232; 351/234; 351/237; 351/239; 351/243
[58] Field of Search ............... 351/222, 232, 237, 239, 351/243, 233, 234; 359/501, 485

[56] References Cited
U.S. PATENT DOCUMENTS

| | | |
|---|---|---|
| 2,206,303 | 7/1940 | Neumueller et al. ............... 351/232 |
| 2,280,297 | 4/1942 | Neumueller et al. ............ 351/232 X |
| 2,933,977 | 4/1960 | Landis ................................. 351/232 |
| 2,976,764 | 3/1961 | Hyde et al. ..................... 359/501 X |
| 5,216,458 | 6/1993 | Andera et al. ...................... 351/243 |

*Primary Examiner*—Anita Pellman Gross
*Assistant Examiner*—David R. Parsons
*Attorney, Agent, or Firm*—Bean, Kauffman & Spencer

[57] ABSTRACT

A device for testing visual contrast sensitivity is disclosed whereby the contrast between a vectographically polarized test symbol and a reference background may be continuously varied by changing the direction of polarization of a polarization analyzer situated along the test axis. The invention is practiced by providing a chart projector or a conventional refractor with a rotatable analyzer.

6 Claims, 5 Drawing Sheets

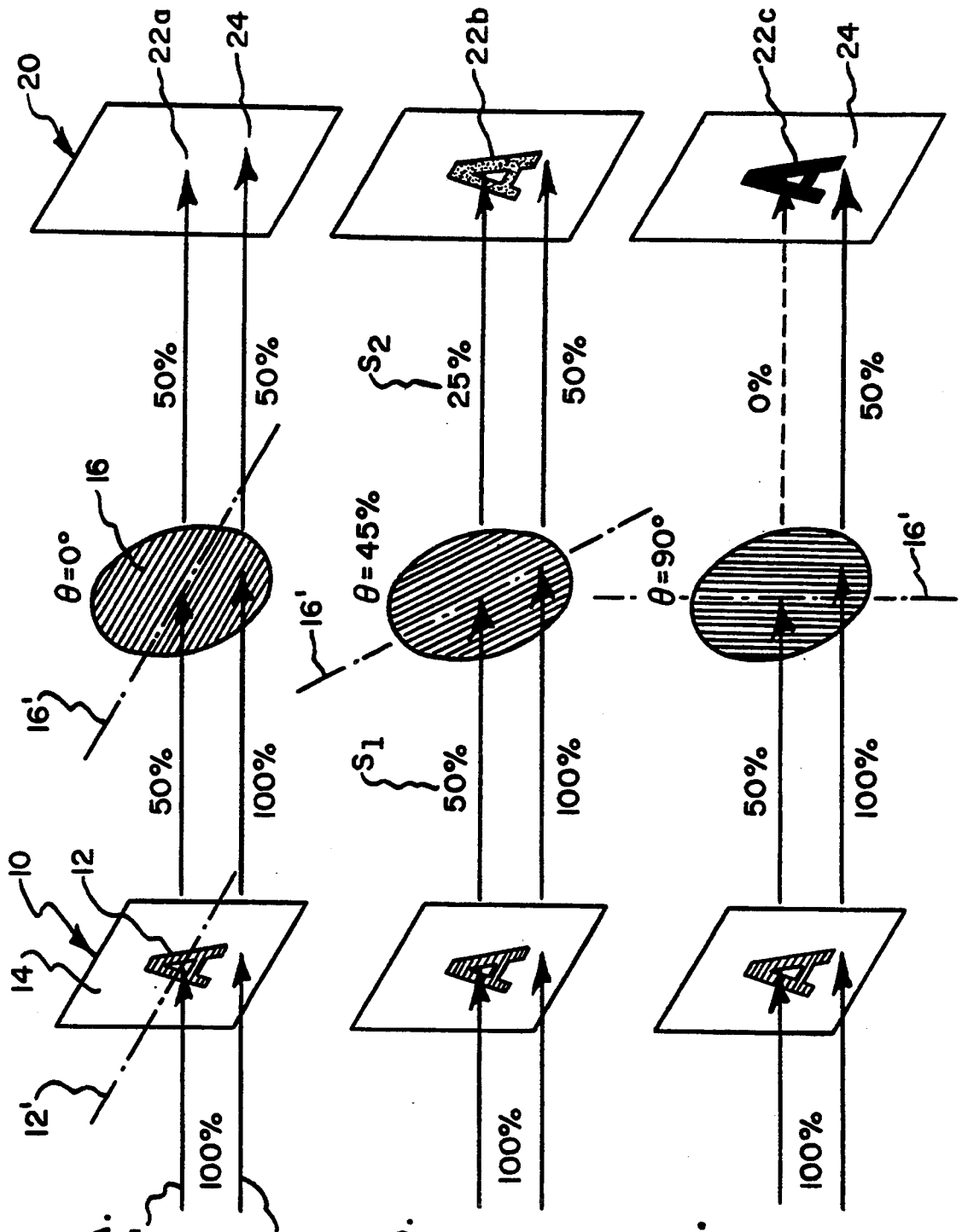

CONTRAST SENSITIVITY TESTER

BACKGROUND OF THE INVENTION

The present invention relates to contrast sensitivity testers and, more particularly, to contrast sensitivity testers using projected images produced by vectographic slides or vectographic near-point cards.

Vectographic slides have been used for many years to test for monocular acuity under binocular conditions, axis of astigmatism of each eye under binocular conditions, acuity and accommodative balance between the right and left eyes, binocular instability, parity between monocular and binocular acuity, muscle balance, fixation disparity, and stereo acuity. One early report on the use of such slides was published in the *New England Journal of Optometry*, May 1966, Vol. XVII, No. 5. The unique feature of these slides is the presence of polarized symbols against an unpolarized background portion; typically, some symbols are polarized in one direction and other symbols are polarized in the orthogonal direction. The traditional tests noted above are conducted using a pair of orthogonal polarization analyzers, one in front of each eye, to make each symbol visible to one eye and invisible to the other eye. Positioning of the analyzers at exactly 90° is not required, since unwanted ghost images do not appear until the analyzers are fully 20° out of alignment. Most subjective refractors are offered to practitioners with orthogonal analyzers mounted in the accessory wheels.

Since most practitioners already use vectographic slides and near-point cards, the adaptation of a refractor to provide rotatable analyzers instead of, or in addition to, the fixed analyzers offers a simple means for contrast sensitivity testing in addition to the conventional vectographic tests. Alternatively, a rotatable analyzer can be added to a chart projector. Vectographic slides and vectographic near-point cards, which may include slides and near-point cards having test symbols polarized in one direction only, may be used in conjunction with rotatable analyzers for testing contrast sensitivity. One advantage of a refractor containing rotatable analyzers is that contrast sensitivity under reading conditions can be tested using vectographic near-point reading cards. Vectographic near-point reading cards for use in binocular refraction, and a process for making them, are disclosed in U.S. Pat. No. 3,572,911 issued Mar. 30, 1971; it will be understood by those skilled in the art that the disclosed process may be easily modified to produce near-point cards having a symbol or symbols polarized in one direction only.

Heretofore, contrast sensitivity testing has been conducted using special charts containing symbols having different contrast levels relative to the chart background or slides that project symbols of different contrast levels. Such devices have the inherent disadvantage that there is necessarily a predetermined finite step between each contrast level, whereby the precision with which contrast sensitivity may be determined is limited.

Thus, it is an object of the present invention to provide an improved means of testing contrast sensitivity whereby the relative contrast of a test symbol in relation to a reference background may be continuously, rather than discretely, varied by the practitioner.

It is a further object of the present invention to provide a means of testing contrast sensitivity using vectographic slides or vectographic near-point cards rather than specialized contrast-level type charts or slides.

Another object is to enable practitioners to conduct an improved test for contrast sensitivity through simple modification of a conventional refractor or chart projector.

Other objects, advantages, and features of the present invention will become apparent from the following description and taken in connection with the accompanying figures.

SUMMARY OF THE INVENTION AND DRAWINGS

The present invention is directed to devices for varying the contrast between a vectographically polarized test symbol and the background surrounding the symbol. The variation can be achieved by including a rotatable analyzer in each bank of a conventional subjective refractor through which a vectographic slide or vectographic near-point card is viewed, or by including a rotatable analyzer in a chart projector used to project a vectographic slide.

DETAILED DESCRIPTION

Figure 1D:
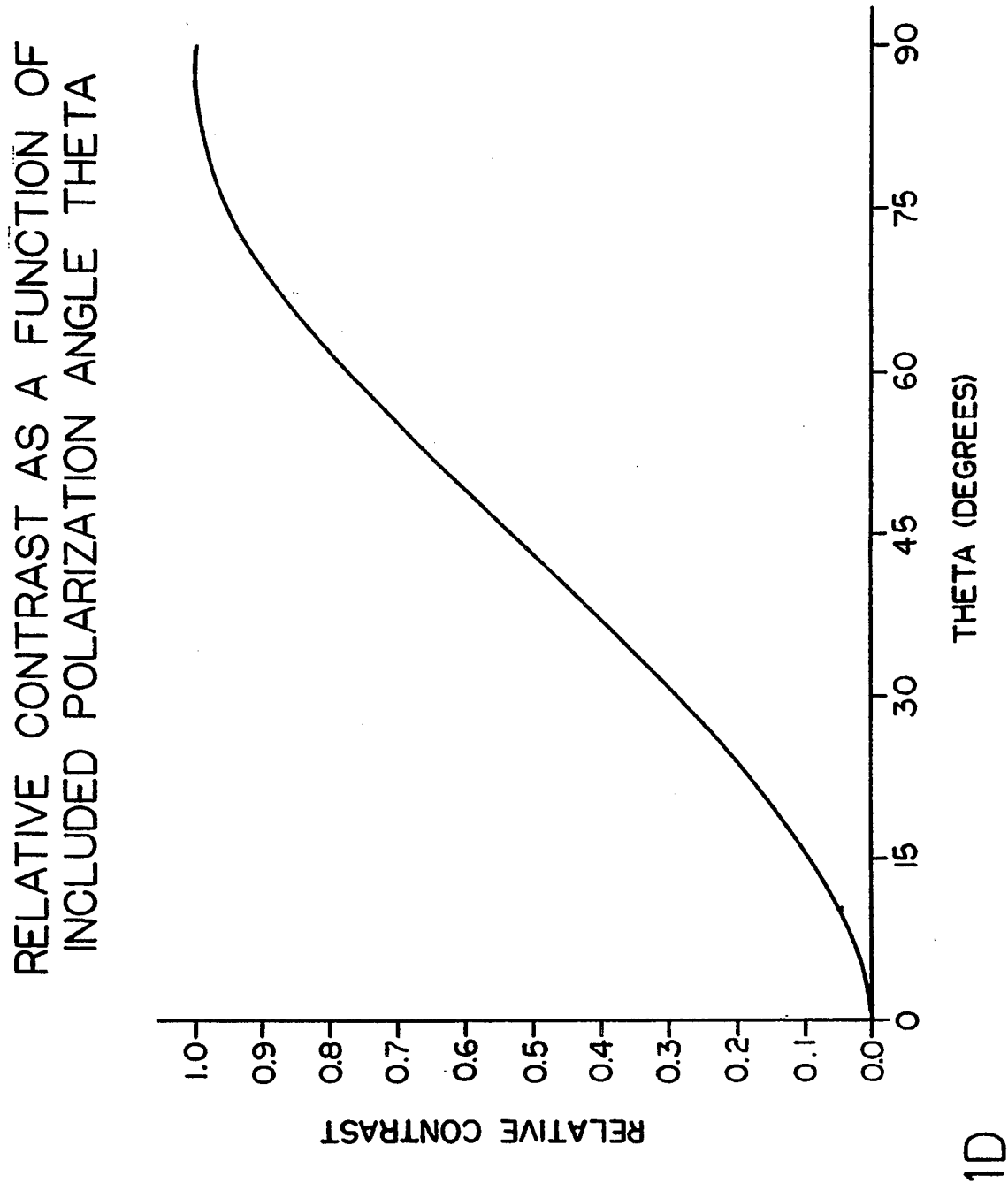
FIGS. 1a, 1b and 1c are graphical representations of a vectographically polarized projected image illustrating the effect of varying the orientation of the analyzer with respect to a FIG. 1d is a graph indicating relative contrast as a function of analyzer orientation for the system illustrated in FIGS. 1a–1c; horizontally polarized test symbol.

The principle of continuous contrast variation with regard to vectographic test symbols is illustrated in FIGS. 1a through 1c. In the simplest contrast situation, concern is solely for two luminance levels: a higher level $L_n$, and a lower level $L_l$. The relative contrast $C_{rel}$ between the two luminance levels may be expressed as the ratio of the difference between the two levels to the higher level:

$$C_{rel} = (L_n - L_l)/L_n$$

where $L_n$ is greater than or equal to $L_l$.

In accordance with the present invention, the lower luminance level $L_l$ is the light transmittance corresponding to the projected test symbol expressed as a percentage of source light, while the higher luminance level $L_n$ is the light transmittance corresponding to the surrounding reference background, also expressed as a percentage of source light. Thus, relative contrast may be expressed by the following relation:

$$C_{rel} = (B - S)/B$$

where S is the light transmittance corresponding to the projected test symbol and B is the light transmittance corresponding to the surrounding reference background. Consequently, a relative contrast value of 0 indicates an absence of contrast between the projected test symbol and the reference background; conversely, a value of 1 indicates maximum contrast between the projected test symbol and the reference background.

Referring to FIG. 1a, projected unpolarized source light, represented by light paths 8', and 8", is intersected by vectographic slide 10, which is orthogonally situated with respect to the incident light. Vectographic slide 10 includes polarized test symbol 12 printed on transparent film 14. Test symbol 12, in the form of uppercase letter A, has a direction of polarization or polarization axis 12' and intersects light path 8'. Direction of polarization 12', shown in FIGS. 1a through 1c as being horizontal for explanatory purposes, may be arbitrarily chosen. The transparent portion of slide 10, which functions to produce a reference background for the projected image of test symbol 12, intersects light path 8". Since unpolarized source light along path 8' can be considered as being half horizontally polarized and half vertically polarized, polarized test symbol 12 transmits only the horizontally polarized portion of the light; consequently, the transmittance through the test symbol is 50 percent and the transmitted light along path 8' becomes horizontally polarized. The transparent portion 14 of vectographic slide 10 transmits 100 percent of unpolarized incident source light along path 8", and the light remains unpolarized.

The light is then intercepted by rotatable polarization analyzer 16, which is orthogonally situated with respect to the incident light. In FIG. 1a, analyzer 16 has a horizontal direction of polarization or polarization axis 16', hence the included angle $\theta$ between test symbol polarization axis 12' and analyzer polarization axis 16' is 0 degrees. At this angle of rotation, analyzer 16 transmits 50 percent of the unpolarized light along path 8" which had been completely transmitted by the transparent reference background 14. The light along path 8' which was horizontally polarized by test symbol 12 is completely transmitted by analyzer 16 where the analyzer polarization axis 16' substantially matches the direction of polarization of the incident light, as shown in FIG. 1a. Consequently, all of the light which has passed through analyzer 16 is of homogeneous intensity corresponding to a 50 percent transmittance of source light.

The light then illuminates display screen 20. Because the transmittance of light for test symbol 12 is equal to the transmittance of light for reference background 14, the relative contrast is zero and projected test symbol image 22a is indistinguishable from projected background 24.

FIG. 1b illustrates the effect of rotating analyzer 16 through an angle of rotation $\theta$ equal to 45 degrees. The reference background transmittance along path 8" remains at 50 percent, while the test symbol transmittance along path 8' varies continuously as a function of the angle of rotation $\theta$ according to the equation $S_2 = S_1 \cos^2 \theta$, where $S_2$ is the test symbol transmittance through analyzer 16 and $S_1$ is the test symbol transmittance through vectographic slide 10, both as a percentage of source light. For $\theta$ equal to 45 degrees, the test symbol transmittance $S_2$ is reduced to 25 percent, resulting in a darkened test symbol image 22b at display screen 20 in relation to projected reference background 24, and the relative contrast becomes 0.5.

If analyzer 16 is further rotated such that $\theta$ equals 90 degrees, as shown in FIG. 1c, a condition of maximum relative contrast is reached. Where analyzer polarization axis 16' is perpendicular to test symbol polarization axis 12', test symbol transmittance along path 8' is eliminated and the relative contrast value is 1 for test symbol image 22c in relation to reference background 24.

The graph in FIG. 1d, represents the continuous variation of relative contrast as included angle $\theta$ is varied from 0 through 90 degrees.

Figure 2:
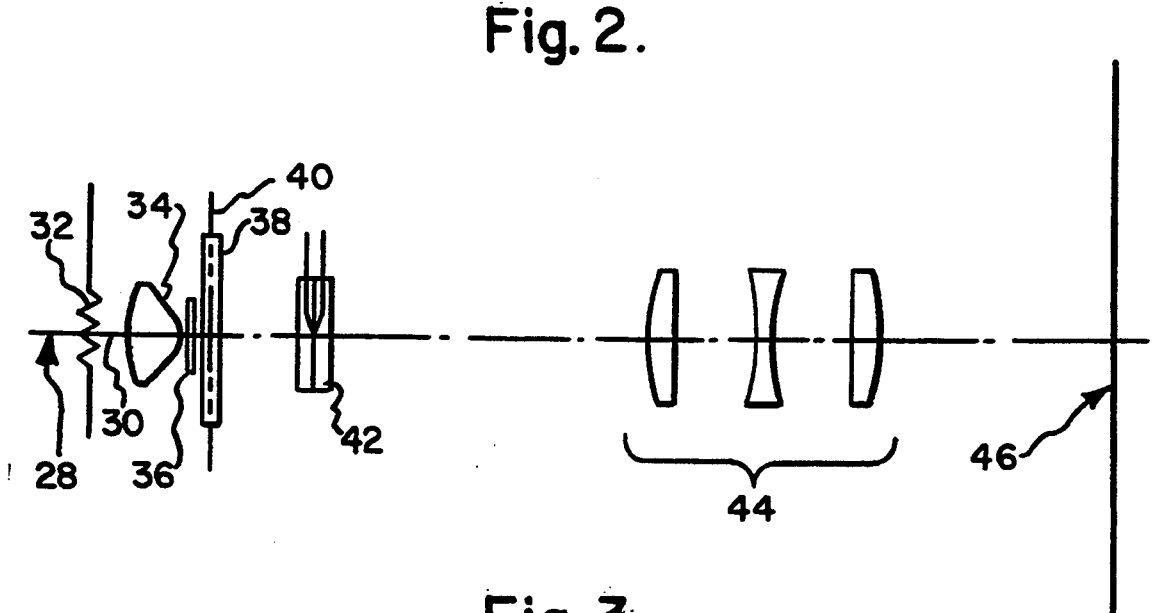
FIG. 2 is an optical schematic diagram of a chart projector in accordance with an embodiment of the present invention.

Referring now to FIG. 2, a schematic representation of a chart projector system in accordance with a preferred embodiment of the present invention is shown. Light source 32, such as the filament of a projection lamp, condensing lens 34, and filter system 36 combine in a known manner to generate light path 30 along projection axis 28. A vectographic slide 38 is orthogonally aligned to intersect light path 30 at film plane 40. Light along light path 30 which is transmitted by vectographic slide 38 is then caused to intersect modifier 42 selectively positioned and oriented orthogonal to the light path. Conventional projection lens 44 is provided to project the resultant image transmitted by the modifier onto screen 46.

Figure 3:
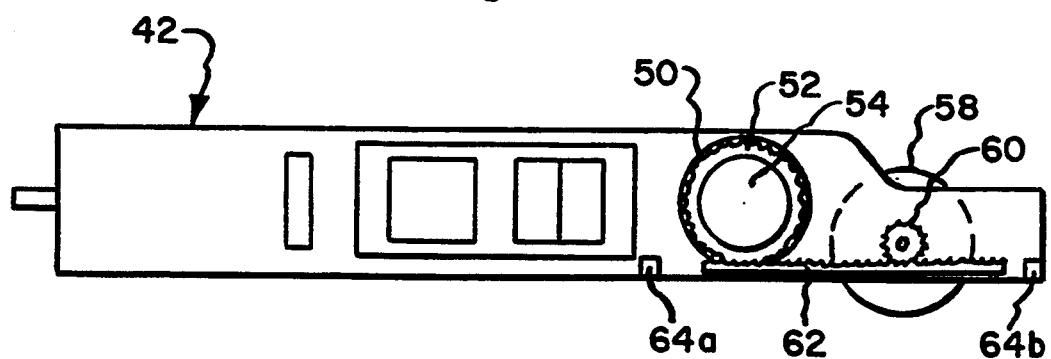
FIG. 3 is a rear view of a modifier slide having a rotatable analyzer.

Modifier 42 is shown more fully at FIG. 3 and includes rotatable polarization analyzer 54 fixed within cell 52, which is rotatably mounted within counterbored seat 50. A conventional rack and pinion assembly is provided to permit rotation of analyzer 54 by a user. Drive knob 58, which is rotatably mounted to modifier 42, drives a concentrically attached pinion gear 60 engaged with rack 62, resulting in linear motion of rack 62 relative to cell 52; teeth on rack 62 mate with peripheral gear teeth on cell 52, causing the cell and analyzer to rotate. The linear motion of rack 62 is limited by limit stops 64a and 64b such that the rotational motion of analyzer 54 is correspondingly restricted to an included angle of 90 degrees. Alternative systems (not shown) are contemplated for rotating the analyzer, such as a drive gear internally mounted on the projector to engage one side of a two-sided rack when the modifier is slid into position and the other side of the rack engaging teeth on the cell, or a lead screw system whereby threads on a knobbed lead screw directly engage worm gear teeth on the periphery of the cell. By varying factors of a particular rotational system, such as gear ratios and/or pitch, suitable speed and precision for rotating analyzer 54 may be achieved. It is also within the scope of the present invention to provide tandem rotatable analyzers on modifier 42 by adding a second cell and analyzer proximate the first cell and analyzer whereby both analyzers may be rotated by the same drive mechanism.

Figure 4:
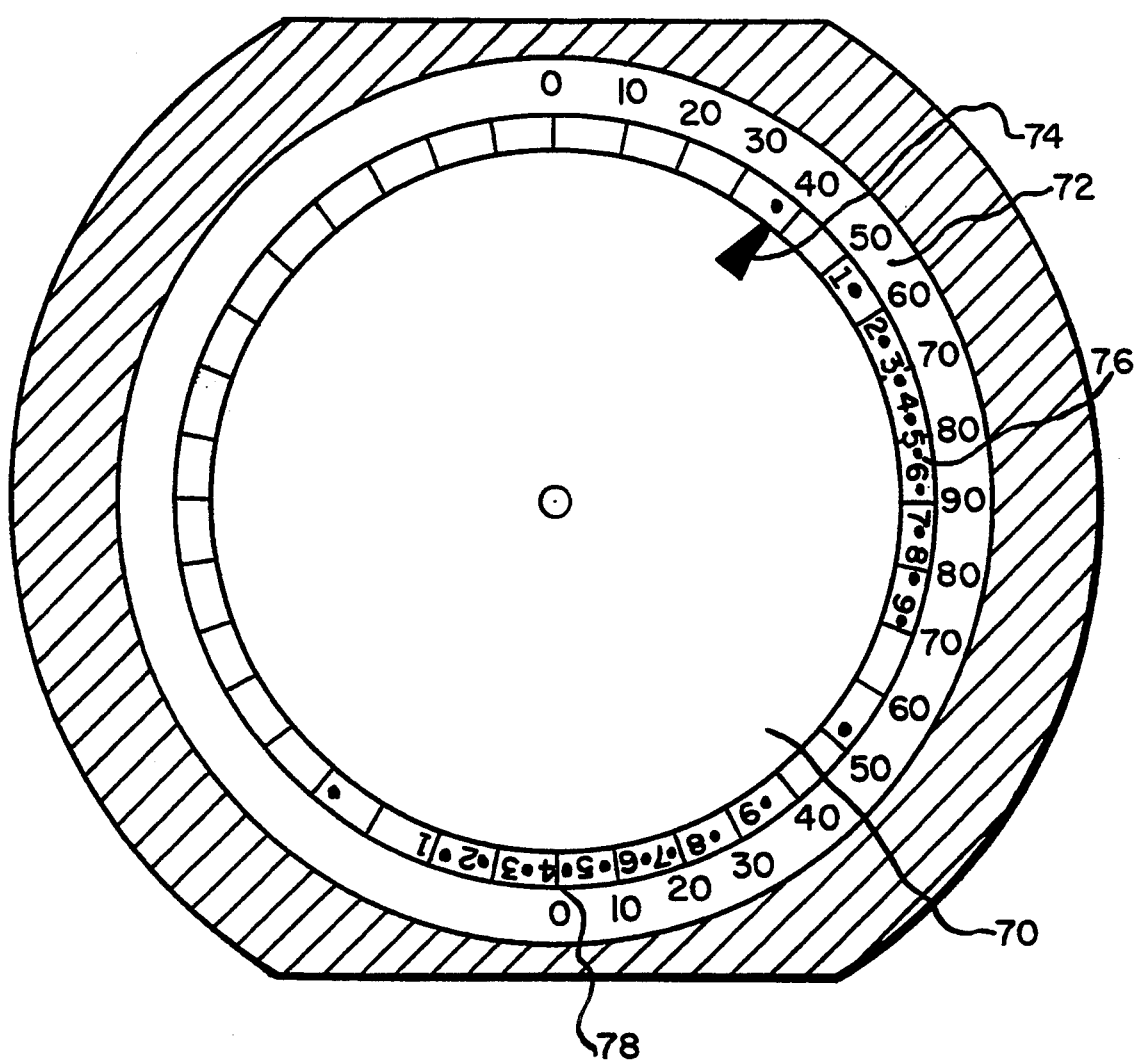
FIG. 4 illustrates an indicator scale for reporting analyzer orientation and relative contrast.

The orientation of the analyzer is preferably indicated as part of the projected image appearing on the screen, thereby enabling the practitioner to easily view a quantitative measure of the patient's contrast sensitivity while administering an examination in a darkened room. Referring to a preferred arrangement illustrated in FIG. 4, the angle of analyzer rotation is generally indicated by a scale marker 74 which is fixed relative to analyzer 70 and which moves relative to stationary radial reference scale 72 as the analyzer is rotated, thereby marking a point on reference scale 72 corresponding to the angular rotation of analyzer 70; a rotation of approximately 38 degrees is shown in FIG. 4. Reference scale 72 is preferably printed on the vectographic chart slide or, in the alternative, on a separate transparency. Projection of scale marker 74 is preferably achieved by providing a shaped cutout in analyzer 70 suitably located with respect to reference scale 72 whereby a relatively bright region will be projected onto the screen at the appropriate reference scale line, or a miniature short focal length lens may be inserted into a circular cutout in analyzer 70 and cemented in place to project a relatively bright spot onto the screen image. In the alternative, a shaped opaque overlay may be encorporated on the analyzer to produce a shadow on the projected image at the appropriate scale line.

An additional scale is preferably provided to allow the examining practitioner to directly obtain a measure of relative contrast that is not expressed in degrees. A contrast scale 76 calibrated in accordance with $\cos^2 \theta$ is shown in FIG. 4, with readings ranging from 0 through 10; other suitable scales, such as linear scales (not shown) ranging from 0 through 10 with each unit equal to 9 degrees of rotation, or one-tenth of the contrast range, may also be employed. Like scale marker 74, calibrated contrast scale 76 is preferably fixed relative to analyzer 70 and moves relative to reference scale 72 as the analyzer is rotated; a reading may be obtained by comparing the contrast scale position in radial alignment with a zero setting 78 on reference scale 72. In the alternative, a calibrated contrast scale may be printed bi-ocularly, and in registry, thereby achieving high optical density.

Figure 5:
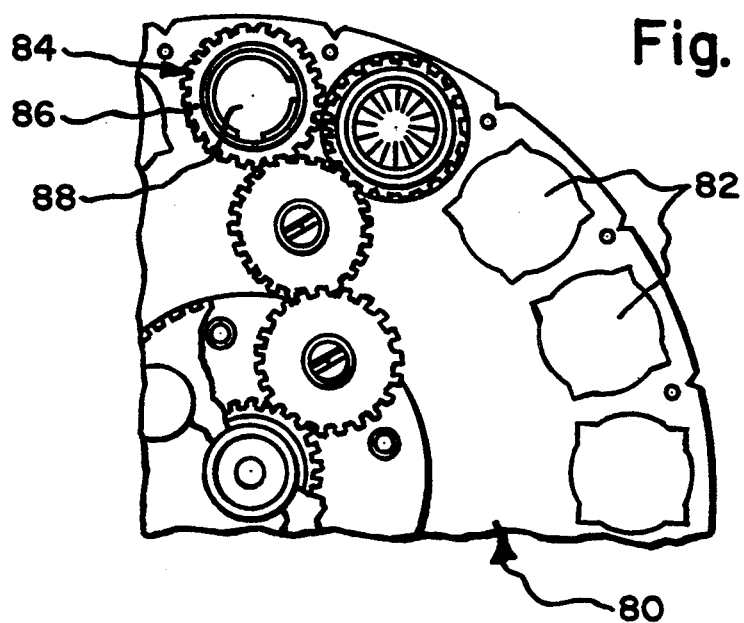
FIG. 5 is a front view of a portion of a rotatable slide disc having a rotatable analyzer.

An alternative embodiment of the present invention is illustrated by FIG. 5 with reference to prior U.S. Pat. No. 3,655,276 issued on Apr. 11, 1972 to Wilkinson, the specification and drawings of which are incorporated herein. U.S. Pat. No. 3,655,276 relates to an ophthalmic refracting chart projector in which slides are mounted peripherally around discs which are rotatable relative to the projector light path such that an operator may selectively place desired slides in the light path by remote control. As described at column 1, line 73 through column 2, line 3, slide apertures disposed around the periphery of a first disc may be equipped, as desired, with rotatable cells for holding certain test slides, for instance a paraboline chart slide. A form of the present invention is carried out by locating a polarization analyzer within a rotatable cell on the first disc and mounting a vectographic slide on a second disc located between the projector light source and the first disc. When the vectographic slide and analyzer are aligned along the projector light path, the analyzer may be rotated to vary the contrast of the projected chart image.

FIG. 5 herein shows a portion of a disc 80 with peripheral apertures 82. A rotatable cell 86 is set into aperture 84 and polarization analyzer 88 is secured within cell 86 to rotate therewith. Rotation of cell 86 is effected by a motor-driven gear train as described in the above-referenced patent at column 2, lines 8-26 and 53-54, and at column 3, lines 21-23.

A further embodiment of the present invention is practiced by rotatably supporting a polarization analyzer in a conventional ophthalmic refractor. A practitioner may then rotate the analyzer to vary the relative contrast of a projected vectographic slide image or a vectographic near-point card as viewed by a test subject.

A conventional refractor is disclosed in prior U.S. Pat. No. 3,498,699 issued Mar. 3, 1970 to Wilkinson, the specification and drawings of which are incorporated herein. The refractor has right and left batteries for enabling the practitioner to position various corrective lenses on a test axis in viewing alignment with the test subject's eyes and a viewing tube, with each battery having a sphere lens assembly and a cylinder lens assembly. As described at column 5, lines 61-76, the practitioner may control the orientation of the cylinder lenses by rotating a cylinder axis control knob.

Figure 6:
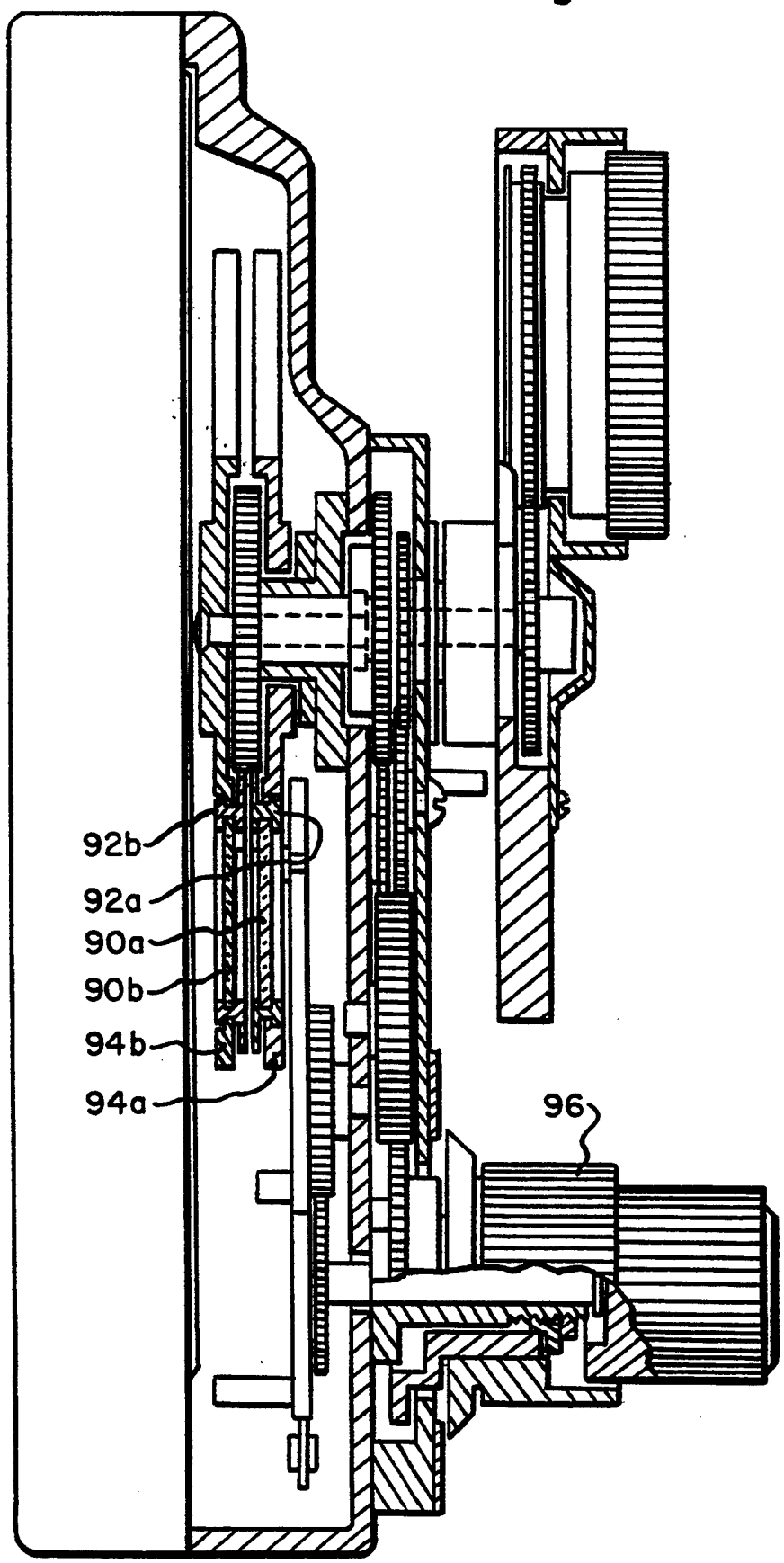
FIG. 6 illustrates one bank of a refractor, partly in section, having external means to rotate a mounted analyzer.

FIG. 6 herein shows a conventional refractor in cross-section. A polarization analyzer is rotatably mounted in either disc 94a or 94b where a cylinder lens typically resides, at either 90a or 90b, by cell 92a or 92b, respectively. Rotatable control knob 96 acts through a gear train to effect rotation of the analyzer, as disclosed in the above-incorporated patent for the case of a cylinder lens. Suitable visual indication of the analyzer's orientation may be provided as described at column 6, lines 29-42 of referenced U.S. Pat. No. 3,498,699.

What is claimed is:

1. A visual acuity chart projector which comprises, a projection axis, a test slide positioned on said axis, said test slide being transparent and having a polarized test symbol and an unpolarized reference background surrounding said test symbol, means for positioning said test slide on said axis, a polarization analyzer positioned on said axis, said analyzer having a direction of polarization, means for positioning said analyzer on said axis, and means for changing the direction of polarization of said analyzer, whereby the contrast between a projected image of said test symbol and a projected image of said reference background is varied by changing the direction of polarization.

2. A chart projector according to claim 1, wherein said test slide further includes a reference scale and said analyzer further includes a reference scale marker coacting with said reference scale, said reference scale and reference scale marker being projected with said test symbol, whereby said direction of polarization is indicated.

3. A visual acuity test system which comprises, a test axis, a corrective lens positioned on said test axis, first support means for positioning said corrective lens on said test axis, a polarization analyzer positioned on said test axis, said analyzer having a direction of polarization, a second support means for positioning said analyzer on said test axis, means for varying the direction of polarization of said analyzer and means for providing a polarized test symbol having a surrounding unpolarized reference background on said test axis, whereby the contrast between said polarized test symbol and said surrounding reference background therefor is varied by changing the direction of polarization of said analyzer for testing visual acuity under varying contrast conditions.

4. A visual acuity test system according to claim 3, wherein said test symbol is a projected image.

5. A visual acuity test system according to claim 3, wherein said means for providing a polarized test symbol includes a vectographic near-point card.

6. A refractor comprising a pair of batteries, each said battery including:
 a test axis;
 a viewing tube aligned on said test axis;
 a sphere lens assembly comprising a plurality of corrective lenses and means for selectively aligning at least one of said corrective lenses with said viewing tube;
 a cylinder lens assembly comprising at least one disc, said disc having a plurality of cells for mounting optical elements therein;

means for rotating said disc for selectively aligning any one of said optical elements with said viewing tube;

a polarization analyzer mounted in one of said cells, said analyzer having a direction of polarization; and means for rotating said analyzer to change the direction of polarization when said analyzer is aligned with said viewing tube;

whereby the contrast between a polarized test symbol and an unpolarized reference background therefor is varied by changing the direction of polarization of said analyzer.

* * * * *